US00RE34515E

United States Patent [19]

Foley

[11] E Patent Number: Re. 34,515

[45] Reissued Date of Patent: Jan. 18, 1994

[54] STEAM STERILIZATION INDICATOR

[75] Inventor: Theodore A. Foley, East Brunswick, N.J.

[73] Assignee: PyMaH Corporation, Somerville, N.J.

[21] Appl. No.: 813,371

[22] Filed: Dec. 24, 1991

Related U.S. Patent Documents

Reissue of:

[64] Patent No.: 4,448,548
Issued: May 15, 1984
Appl. No.: 47,955
Filed: Jun. 11, 1979

[51] Int. Cl.[5] ..... G01N 31/02; C09K 3/00; G12Q 1/22; A23L 3/00

[52] U.S. Cl. ..... 374/160; 252/408.1; 374/162; 422/58; 426/88; 435/31

[58] Field of Search ..... 374/160, 162; 252/408.1; 422/57, 58; 435/31; 426/88; 116/207, 216, 217, 218, 219, 220

[56] References Cited

U.S. PATENT DOCUMENTS

| | | | |
|---|---|---|---|
| 161,118 | 3/1875 | Halvorson . | |
| 197,902 | 12/1877 | Scott . | |
| 1,000,673 | 8/1911 | Diack . | |
| 1,191,572 | 7/1916 | Davis . | |
| 1,238,123 | 8/1917 | Freeman . | |
| 1,426,569 | 8/1922 | Ingram . | |
| 1,441,307 | 1/1923 | Swanberg . | |
| 1,535,536 | 4/1925 | MacDonald . | |
| 1,558,153 | 10/1925 | Ferkel . | |
| 1,676,536 | 7/1928 | Ferkel . | |
| 1,703,880 | 5/1929 | Gordon . | |
| 1,788,104 | 1/1931 | Hargreaves . | |
| 1,843,234 | 2/1932 | Karnes et al. . | |
| 1,894,015 | 1/1933 | Bernstein . | |
| 1,917,048 | 7/1933 | Midgley . | |
| 1,951,650 | 3/1934 | Diack . | |
| 2,046,863 | 7/1936 | Allphin | 73/32 |
| 2,049,867 | 8/1936 | Richards | 40/2 |
| 2,118,144 | 5/1938 | Berman et al. | 73/356 |
| 2,195,395 | 4/1940 | Chapman | 23/5 |
| 2,222,067 | 11/1940 | Chaney et al. | 116/114 |
| 2,269,038 | 1/1942 | Perry | 116/114 |
| 2,277,278 | 3/1942 | Triplett | 99/192 |
| 2,278,749 | 3/1942 | Beckett et al. | 116/114 |
| 2,308,087 | 1/1943 | Lappala | 73/356 |
| 2,335,999 | 12/1943 | Diack | 73/358 |
| 2,337,534 | 12/1943 | Barber | 35/1 |
| 2,379,459 | 7/1945 | Schreiber et al. | 73/358 |
| 2,460,215 | 1/1949 | Chase | 99/192 |
| 2,490,933 | 12/1949 | Tornquist et al. | 73/358 |
| 2,552,477 | 5/1951 | Cole | 73/193 |
| 2,560,537 | 7/1951 | Andersen | 99/192 |
| 2,567,445 | 9/1951 | Parker | 23/230 |
| 2,579,738 | 12/1951 | Hargreaves | 73/358 |

(List continued on next page.)

*Primary Examiner*—Peter Kratz
*Attorney, Agent, or Firm*—Robert H. Falk; Tom R. Vestal

[57] ABSTRACT

An improved steam sterilization indicator is provided. The indicator includes a fusible material in tablet form, deposited in an embossment in one end of a thin aluminum backing. A wicking strip is attached to the backing with one end of the strip being in close proximity to the fusible tablet. A clear plastic material covers the tablet and the strip and is adhered to the backing. The melting point of the fusible tablet is depressed in the presence of saturated steam. Upon melt, the material in the tablet is absorbed by the wicking strip, producing a color front to provide an indication of the integration of time and temperature in the presence of steam. Various amounts of a binder are used in the tablet to provide a device which may be adjusted to reflect the thermal death curves of various types of microorganisms. The cover and the wick are bonded to the backing by an acyclic adhesive which also affects the rate of the indicator.

13 Claims, 2 Drawing Sheets

U.S. PATENT DOCUMENTS

| | | | |
|---|---|---|---|
| 2,606,654 | 8/1952 | Davis et al. | 206/47 |
| 2,614,430 | 10/1952 | Ballard et al. | 73/358 |
| 2,677,278 | 5/1954 | Smith et al. | 73/358 |
| 2,708,896 | 5/1955 | Smith et al. | 116/114 |
| 2,716,065 | 8/1955 | Beckett et al. | 99/192 |
| 2,798,855 | 7/1957 | Hainsworth | 252/408 |
| 2,798,856 | 7/1957 | Hainsworth | 252/408 |
| 2,799,167 | 7/1957 | Loconti | 73/356 |
| 2,826,073 | 3/1958 | Huyck et al. | 73/356 |
| 2,847,067 | 8/1958 | Brewer | 161/15 |
| 2,850,393 | 9/1958 | Romito | 99/192 |
| 2,854,384 | 9/1958 | Beakley | 195/54 |
| 2,889,799 | 6/1959 | Korpman | 116/114 |
| 2,915,405 | 12/1959 | Hammond et al. | 99/192 |
| 2,918,893 | 12/1959 | Norton | 116/114 |
| 2,928,791 | 3/1960 | Loconti | 252/408 |
| 2,932,971 | 4/1960 | Moore et al. | 73/356 |
| 2,951,764 | 9/1960 | Chase | 99/192 |
| 2,971,852 | 2/1961 | Schulein | 99/192 |
| 2,998,306 | 8/1961 | Huyck et al. | 23/254 |
| 3,002,385 | 10/1961 | Wahl et al. | 73/356 |
| 3,018,611 | 1/1962 | Biritz | 58/1 |
| 3,046,786 | 7/1962 | Tessem | 73/356 |
| 3,047,405 | 7/1962 | Lanier | 99/192 |
| 3,055,759 | 9/1962 | Busby et al. | 99/192 |
| 3,059,474 | 10/1962 | Keller et al. | 73/358 |
| 3,065,083 | 11/1962 | Gessler | 99/192 |
| 3,067,015 | 12/1962 | Lawdermilt | 23/253 |
| 3,078,182 | 2/1963 | Crone, Jr. et al. | 117/68.5 |
| 3,082,624 | 3/1963 | Renier | 73/356 |
| 3,093,242 | 6/1963 | Huyck et al. | 206/47 |
| 3,098,751 | 7/1963 | Huyck et al. | 106/20 |
| 3,114,349 | 12/1963 | Schuman | 116/114 |
| 3,118,774 | 1/1964 | Davidson et al. | 99/192 |
| 3,205,158 | 9/1965 | Renier | 204/195 |
| 3,242,733 | 3/1966 | Johnson | 73/344 |
| 3,243,303 | 3/1966 | Johnson | 99/192 |
| 3,288,718 | 11/1966 | Carumpalos | 252/408 |
| 3,311,084 | 3/1967 | Edenbaum | 116/114 |
| 3,313,266 | 4/1967 | Kelson | 116/114 |
| 3,324,723 | 6/1967 | Ritchie | 73/358 |
| 3,341,238 | 9/1967 | White | 289/1.5 |
| 3,344,670 | 10/1967 | Olsen et al. | 73/356 |
| 3,352,794 | 11/1967 | Abdo | 252/408 |
| 3,360,337 | 12/1967 | Edenbaum et al. | 23/253 |
| 3,360,338 | 12/1967 | Edenbaum | 23/253 |
| 3,360,339 | 12/1967 | Edenbaum | 23/253 |
| 3,386,807 | 6/1968 | Edenbaum | 23/253 |
| 3,399,284 | 8/1968 | Morison | 200/61.05 |
| 3,414,415 | 12/1968 | Broad | 99/192 |
| 3,420,205 | 1/1969 | Morison | 116/114 |
| 3,430,491 | 3/1969 | Gignilliat | 73/358 |
| 3,437,070 | 4/1969 | Campbell | 116/114 |
| 3,440,144 | 4/1969 | Andersen | 195/103.5 |
| 3,460,964 | 8/1969 | Dunham | 117/36.9 |
| 3,465,590 | 9/1969 | Kulth et al. | 73/356 |
| 3,471,422 | 10/1969 | Edlein et al. | 260/22 |
| 3,479,877 | 11/1969 | Allen et al. | 73/358 |
| 3,523,011 | 8/1970 | Bhiwandker et al. | 23/253 |
| 3,545,400 | 12/1970 | Smith | 116/114.5 |
| 3,580,079 | 5/1971 | Crites et al. | 73/358 |
| 3,597,976 | 8/1971 | Fryar | 73/358 |
| 3,616,898 | 11/1971 | Williams | 206/56 AA |
| 3,620,677 | 11/1971 | Morison | 23/253 |
| 3,627,469 | 12/1971 | Chang | 23/232 R |
| 3,652,249 | 3/1972 | White | 65/156 |
| 3,661,717 | 5/1972 | Nelson | 195/103.5 R |
| 3,665,770 | 5/1972 | Sagi et al. | 73/356 |
| 3,667,916 | 6/1972 | Sliva et al. | 23/230 R |
| 3,684,737 | 8/1972 | Emigh | 252/408 |
| 3,695,903 | 10/1972 | Telkes et al. | 99/192 TT |
| 3,704,985 | 12/1972 | Pickett et al. | 73/356 |
| 3,718,815 | 2/1973 | McDonough | 240/1.3 |
| 3,768,976 | 10/1973 | Hu et al. | 23/254 R |
| 3,843,452 | 10/1974 | Freake et al. | 195/103.5 |
| 3,846,242 | 11/1974 | Ernst | 195/103.5 |
| 3,862,824 | 1/1975 | Chapman | 23/253 TP |
| 3,895,523 | 7/1975 | Nollen | 116/220 |
| 3,932,134 | 1/1976 | Fang et al. | 23/253 TP |
| 3,935,743 | 2/1976 | Brodie | 374/160 |
| 3,942,467 | 3/1976 | Witonsky | 116/114 V |
| 3,946,611 | 3/1976 | Larsson | 73/356 |
| 3,954,011 | 5/1976 | Manske | 73/356 |
| 3,962,920 | 6/1976 | Manske | 73/356 |
| 3,981,683 | 9/1976 | Larsson et al. | 23/253 TP |
| 4,038,873 | 8/1977 | Kimmel | 73/358 |

(List continued on next page.)

FOREIGN PATENT DOCUMENTS

| | | |
|---|---|---|
| 141266 | 3/1949 | Australia . |
| 407208 | 8/1968 | Australia . |
| 425236 | 7/1970 | Australia . |

(List continued on next page.)

OTHER PUBLICATIONS

A. Hoyt, "Studies on Rubber Glove Sterilization and the Use of Sterility Indicators", J. Lab. Clin. Med. at 382–390 (1934).

(List continued on next page.)

U.S. PATENT DOCUMENTS

| | | | |
|---|---|---|---|
| 4,042,336 | 8/1977 | Larsson | 23/253 TP |
| 4,145,186 | 3/1979 | Andersen | 23/232 R |
| 4,179,397 | 12/1979 | Rohowetz et al. | 252/408 |
| 4,195,186 | 3/1979 | Andersen | 374/162 |
| 4,333,339 | 6/1982 | McNeely | 116/219 |
| 4,382,063 | 8/1983 | Romito | 374/162 |
| 4,410,493 | 10/1983 | Joslyn | 116/219 |

FOREIGN PATENT DOCUMENTS

| | | |
|---|---|---|
| 625917 | 12/1962 | Belgium . |
| 498481 | 12/1953 | Canada . |
| 823264 | 12/1965 | Canada . |
| 917548 | 12/1972 | Canada . |
| 976741 | 10/1975 | Canada . |
| 994221 | 8/1976 | Canada . |
| 2134314 | 7/1971 | Fed. Rep. of Germany . |
| 1461252 | 10/1966 | France . |
| 45-17039 | 2/1967 | Japan . |
| 49-20385 | 4/1973 | Japan . |
| 425276 | 5/1967 | Switzerland . |
| 551783 | 3/1943 | United Kingdom . |
| 602753 | 6/1948 | United Kingdom . |
| 647379 | 6/1950 | United Kingdom . |
| 889573 | 2/1962 | United Kingdom . |
| 910520 | 11/1962 | United Kingdom . |
| 1026950 | 4/1966 | United Kingdom . |
| 1027417 | 4/1966 | United Kingdom . |
| 1132334 | 10/1968 | United Kingdom . |
| 1212859 | 11/1970 | United Kingdom . |
| 1215891 | 12/1970 | United Kingdom . |
| 1360861 | 7/1974 | United Kingdom . |
| 1367703 | 9/1974 | United Kingdom . |
| 1415782 | 11/1975 | United Kingdom . |

OTHER PUBLICATIONS

C. W. Walter, "An Evaluation of Sterility Indicators", 2 Surgery at 585-589 (1937).

E. E. Ecker, "Sterilization Based on Temperature Attained and Time Ration", 48 Modern Hospital at 86-90 (1937).

W. B. Underwood, "Methods of Testing", A Textbook of Sterilization at 98-105 (1941).

O. Rahn, "Physical Methods of Sterilization of Microorganisms", 1 Bacteriological Reviews at 1-47 (1945).

Ernest O. McCulloch, "Bacteriological and Surgical Sterilization by Heat", Disinfection and Sterilization at 69-105 (1945).

Carl W. Walter, "Sterilization by Dry Heat", The Aseptic Treatment of Wounds at 92-96 (1948).

L. F. Ortenzio, L. S. Stuart and J. L. Friedl, "The Resistance of Bacterial Spores to Constant Boiling Hydrochloric Acid", 36 Journal of the Assoc. of Official Agricultural Chemists at 480-485 (1953).

J. H. Brewer and C. B. McLaughlin, "A Device for Determining Time and Temperature of Sterilization in the Autoclave or Hot-Air Oven", 120 Science at 501-502 (1954).

Lawrence P. Garrod, "Sterilization Methods", British Medical Journal at 350-351 (1955).

J. W. Howie and Morag C. Timbury, "Laboratory Tests of Operating-Theatre Sterilizers", Lancet at 669-673 (1956).

A. C. Scott and M. B. Glasg, "Gravity Air-Displacement Pressure Steam Sterilizers", Lancet at 633-637 (1957).

V. G. Adler and W. A. Gillespie, "The Sterilization of Dressings", 10 J. Clin. Path. at 299-306 (1957).

Agnes H. S. Brown and George Smith, "The Genus Paecilomyces Bainier and its Perfect Stage Byssochlamys Westling", 40(1) Transactions British Mycological Society at 17-89 (1957).

J. C. Kelsey, "The Testing of Sterilizers", 1 Lancet at 306-309 (1958).

E. M. Darmady, K. E. A. Hughes and J. D. Jones, "Thermal Death-Time of Spores in Dray Heat", 2 Lancet at 766-769 (1958).

*Diack Sterilizer Controls.* "Smith & Underwood" advertisement for Diack Control, 92 Modern Hospital at 8 (1959).

*Inform Controls,* "Smith & Underwood" advertisement for Inform Controls, 93 Modern Hospital at 6 (1959).

*Weckink Control,* "Edward Weck & Company" advertisement for Weck Catheter Sterilizing Papers, 93 Modern Hospital at 182 (1959).

J. W. Howie, "Sterilization by Steam Under Increased Pressure", 1 Lancet at 425-435 (1959).

*Scotch Hospital Tapes,* "Minnesota Mining and Manufacturing Company" advertisement for Scotch Brand Hospital Tapes by Minnesota Mining and Manufacturing Company, 92 Modern Hospital at 113 (1959).

*ATI Steriline Bags,* "Aseptic-Thermo Indicator Com- (List continued on next page.)

OTHER PUBLICATIONS pany" advertisement for A.T.I. sterilization aids including Steam-Clox Indicators, Steriline Bags and Tubing, 92 Modern Hospital at 142 (1959).

*Diack Sterilizer Controls*, "Smith & Underwood" Ad for Diack Controls, 92 Modern Hospital at 10 (1959).

G. R. Wilkinson, "The Correlation of Oven Testing and Field Storage of Pharmaceutical Products", 35 Pharm. Acta. Helv. at 327-332 (1959).

*ATI Steam-Clox*, "Aseptic Thermo Indicator Company" advertisement for ATI Steam-Clox Control", 94 Modern Hospital at 184 (1960).

*Pro-Tex-Mor Medical Division*, "Central States Paper & Bag Co." advertisement for Sterilizer Bags with Indicator Marks", 38 Hospital Topics at 115 (1960).

*ATI Steriline Bags*, "Aseptic-Thermo Indicator Company", advertisement for Steriline Bags, 95 Modern Hospital at 120 (1960).

G. R. Wilkinson, G. F. Peacock and E. L. Robins, "A Shorter Sterilizing Cycle for Solutions Heated in an Autoclave", 12 Supp. J. Pharm. Pharmacol. at 197T-202T (1960).

G. R. Wilkinson, "The Correlation of Oven Testing and Field Storage of Pharmaceutical Products", 85 Pharmaceutica Acta Helvetiae at 327-332 (1960).

J. C. Kelsey, "The Testing of Sterilizers", 14 J. Clin. Path. at 313-319 (1961).

*Diack Sterilizer Control*, "Smith & Underwood" advertisement for Diack Controls, 96 Modern Hospital at 10 (1961).

G. R. Wilkinson and F. G. Peacock, "The Removal of Air During Autoclave Sterilization of Fabrics Using Low Pressure Steam", 13 J. Pharm. Pharmacol. Suppl. at 67T-71T (1961).

*Aseptic-Thermo Indicator Company (ATI)*, "Aseptic--Thermo Indicator Company", advertisement for Hi--Temp Indicators, 97 Modern Hospital at 116 (1961).

*Aseptic-Thermo Indicator Company (ATI)*, "Aseptic--Thermo Indicator Company", advertisement for ATI Steriline Bags and Diack Controls, 97 Modern Hospital at 107 (1961).

G. R. Wilkinson and F. G. Peacock, "Improvement of Heating of Bottled Fluirds During Autoclave Sterilization Using Low Pressure Steam", 13 Supp. J. Pharm. Pharmacol. at 72T-74T (1961).

*Dennison MFG. Co.*, "Dennison Manufacturing Company" advertisement for Dennison Wrap Autoclave Tape, 97(4) Modern Hospital at 233 (1961).

*Diack Sterilizer Controls*, "Smith & Underwood" advertisement for Diack Controls, 98 Modern Hospital at 10 (1962).

*TSI Tape*, "Professional Tape Co., Inc." advertisement for TSI Tape, 98(3) Modern Hospital at 125 (1962).

G. R. Wilkinson and F. G. Peacock, "Thermocouples for Autoclaves", 1 The Lancet at 488 (1962).

*ATI Steam-Clox*, "Aseptic-Thermo Indicator Companuy" advertisement for Steam-Clox Indicator", 40 Hospital Topics at 55 (1962).

*Sterilometer*, "Sterilometer Laboratories, Inc." advertisement for Sterilometer, 41(12) Hospital Topics at 74 (1963).

*Sterilometer*, "Sterilometer Laboratories, Inc." advertisement for Sterilometer, 1(2) Aorn Journal at 86 (1963).

*Spordex*, "American Sterilizer" advertisement for Sporde-X Spore Strips, 100 Modern Hospital at 5 (1963).

*3M Autoclave Tape*, "Minnesota Mining and Manufacturing Company" advertisement for 3M Autoclave Tape, 100(5) Modern Hospital at 141 (1963).

*Vac Sterilizer Controls (Diack)*, "Diack Controls" advertisement for VAC Sterilizer Control, 101 Modern Hospital at 10 (1963).

J. H. Bowie, J. C. Kelsey and G. R. Thompson, "The Bowie and Dick" Autoclave Tape Test, 1 The Lancet at 586-587 (1963).

T. B. Owen, J. J. Perkins, A. S. Irons, A. W. Reichert and S. J. Mannarino, "Prevacuum High Temperature Steam Sterilization", 1 The Journal of Hospital Research, 5-30 (1963).

A. Vecchi, "Il Controllo Di 'Sterilita' Sui Prodotti Farmaceutici Industriali", XIX(6) Il Farmaco at 265-275 (1964).

G. R. Wilkinson and L. C. Baker, "Modern Trends in Steam Sterilization", 5 Progr. Industr. Micro-Biol. at 231-282 (1964).

*Biospore Biological Sterility Indicators*, "Castle, Subsidiary of Ritter Company, Inc." advertisement for Spore Controls, 42(3) Hospital Topics at 13 (1964).

G. R. Wilkinson and L. C. Baker, "Contemporary Trends in Heat Sterilization", Advances in Pharm. Sci., vol. I, at 269-314 (1964).

G. R. Wilkinson and D. E. Simpkins, "A Physical Indi- (List continued on next page.)

OTHER PUBLICATIONS cator for Sterilization Procedures", 16 Suppl. J. Pharm. Pharmacol. at 108T-110T (1964).

Sydney D. Rubbo and Joan F. Gardner, *A Review of Sterilization and Disinfection*, Year Book Medical Publishers, Inc. at 6-65 (1965).

G. Sykes, *Disinfection and Sterilization*, 2nd Ed., J. B. Lippincott Company, at 121-145 (1965).

G. Sykes, *Disinfection and Sterilization*, 2nd Ed., "Methods of Sterilization" at 108-119 (1965).

Dr. W. A. Ritschel, "Die Tablette", Grundlagen und Praxis des Tablettierens, Granulierens und Dragierens (and translation, Principles and Practical Aspects of Tablet Formation, Granulation and Coating), 7 Der Pharmazeutische Betrieb at 103-104 (1966).

J. C. Kelsey, "The Bowie-Dick Test", 2 The Lancet at 911-912 (1966).

Carl W. Lawrence and Seymour S. Block, "Sterilization by Heat", Disinfection, Sterilization and Preservation at 714-734 (1968).

I. J. Pflug, "Some Observations Regarding Factors Important in Dry Heat Sterilization", COSPAR Technique Manual No. 4 at 51-58 (1968).

H. F. Struppe, "Untersuchungen zur Eignung von Sterilisationsindikatoren fur Schnellautoklaven", 152(4) Arch. Hyg. Bakteriol at 360-365 (1968).

Thomas Laskaris and Albert L. Chaney, "Reliability of Biologic Autoclave Sterilization Indicators" 52(4) The American Journal of Clinical Pathology at 495-500 (1969).

Frances L. Clapp, "Panel Discussion: Proposed Changes in the USP—Microbiological Aspects", 23 Bulletin of the Parenteral Drug Assoc. at 252-262 (1969).

Karl Kereluk and Robert S. Lloyd, "Ethylene Oxide Sterilization" (American Sterilizer Company), 7 The Journal of Hospital Research at 55-59 (1969).

J. J. Perkins, "Principles and Methods of Sterilization", *Principles and Methods of Sterilization in Health Sciences*, 2nd Ed., selected pages, particularly 488-493 (1969).

Charles Artandi, "Biological Indicators" (Ethicon, Inc.), 23 Bulletin Parenteral Drug. Assoc. at 254-257 (1969).

Larry Day, et al., "Panel Discussion: Biological Indicators—Manufacture and Quality Control for a Biological Indicator", *Bulletin Parenteral Drug Assoc.* (1970).

B. Litsky, "Studies on the Performance of Sterilizer Control Devices Under Experimental Conditions", Smith & Underwood (1970).

Wm. S. Miller, "Panel Discussion: Biological Indicators—(IV) Types of Biological Indicators Used in Monitoring Sterilization Processes", 25 Bulletin of the Parenteral Drug Assoc. at 80-86 (1971).

Frances W. Bowman, "Panel Discussion: Biological Indicators—(III) Quality Control of Biological Indicators", 25 Bulletin of the Parenteral Drug Assoc. at 78-79 (1971).

Armand Marinaro, "Panel Discussion: Biological Indicators—(II) Development of a Biological Indicator Program", 25 Bulletin of the Parenteral Drug Assoc. at 75-77 (1971).

John E. Doyle, "Sterility Indicator with Artificial Resistance to Ethylene Oxide", 25 Bulletin of the Parenteral Drug Assoc. at 98-104 (1971).

Irving J. Pflug. "Sterilization of Space Hardware" (University of Minnesota), 1 Environmental Biology and Medicine at 63-81 (1971).

Arthur D. Little, Inc., "A Study of the Requirements, Preliminary Concepts and Feasibility of a New System to Process Medical/Surgical Supplies in the Field" (U.S. Army Medical Research and Development Command), National Technical Information Service, U.S. Department of Commerce, Report No. 72688 (1971).

Thomas Macek, "Some Thoughts on Sterilization and Sterility Control", 25(1) Bulletin of the Parenteral Drug Assoc. (1971).

Wm. A. Altemeier, "The Significance of Infection in Trauma", Scudder Oration on Trauma at 7-16 (1971).

J. K. Pickerill and R. Perera, "Air Detection in Dressings Steam Sterilizers", 20 Laboratory Practice at 406-413 (1971).

G. Reybrouck and H. Van De Voorde, "Evaluatie Van Sterilisatie-Indicatoren Voor Gebruik InDe Autoclaaf" (and translation), 29(4) Arch. Belg. Med. Soc. at 254-258 (1971).

Pijck, "A New Biological Indicator System for Testing Sterilization Efficiency (English), 26(2) J. De Pharmacie De Belgique at 211-212 (1971).

John J. Mayernik, "Biological Indicators for Steam Sterilization—A U.S.P. Collaborative Study", 26 Bulletin of the Parenteral Drug Assoc. at 205-211 (1972).

Robert F. Smith, "Quality Assurance in Hospital Steam (List continued on next page.)

OTHER PUBLICATIONS

Sterilization", Smith & Underwood Laboratories (1972).

I. J. Pflug, "Heat Sterilization", Industrial Sterilization at 239-281 (1972).

Thomas J. Macek, "Biological Indicators, A U.S.P. Review", 26(1) Bulletin of the Parenteral Drug Assoc. (1972).

S. Stanley Schneierson and edited by R. B. Roberts, "Sterilization by Heat", 10(2) Infections and Sterilization Problems at 67-83 (1972).

H. P. Werner and Ch. Vutuc, "Die Eignung Von Chemischen Und Biologischen Indikatoren Zur Uberprufung Des Sterilisationeffektes Von Autoklaven" (Chemical and Biological Indicators for Monitoring Sterilization in Autoclaves), Zentralblatt at 561-568 (1972).

Rex O. Astrid and Zunino V. Hugo, "Chemical Monitors of Autoclave Sterilization (Translation), 100 Revista Medica de Chile at 1087-1090 (1972).

*Propper Mgf.*, "Propper Sterilization Indicators", 24 Hospital Topics (1973).

*Time Duo-Strip*, "Professional Tape Company, Inc." 73 Hospital Topics (1973).

*Surgicot, Inc.*, "Sterilization Bag" advertisement, 3 Hospital Topics at 67 (1973).

W. A. Hennig, H. S. Stern, R. J. Laza and Y. S. Murthy, "Use of *Bacillus stearothermophilus* as a Biological Indicator", 1 Bulletin of the Parenteral Drug Assoc. at 30-37 (1973).

D. Hugh Starkey and Clifton K. Himmelsback, "On the Avoidance of Failures in Sterilization", Hospitals at 143-152 (1974).

Frank B. Engley, "Discusses Sterilization, Disinfection, Antisepsis for Infection Control", Hospital Topics at 61-69 (1974).

Earle H. Spaulding, "Uses and Abuses of Disinfectants", 5 Hospital Topics at 7-8 (1974).

*E.O. Indicators* (ATI Company), "Performance Certified E.O. Indicators", Hospital Topics at 72 (1974).

C. W. Bruch, "Levels of Sterility Probabilities of Survivors vs. Biological Indicators", 28 Bulletin of the Parenteral Drug Assoc. at 105-121 (1974).

K. Kereluk and R. Gammon, "A Comparative Study of Biological Indicators for Steam Sterilization", 15 Developments in Industrial Microbiology at 411-416 (1974).

J. H. Bowie, "Bowie and Dick Test", I The Lancet at 1233 (1974).

Robert F. Smith, "Modified Bowie-Dick Test", I The Lancet at 1349 (1974).

Michael Korczynski, C. L. Peterson and C. C. Loshbaugh, "An Approach to Establishing Parenteral Solution Sterilization Cycles", 28 Bulletin of the Parenteral Drug Assoc. at 270-277 (1974).

Jan Hoborn, "Steam Sterilization: A Comparison of Steam-Clox and Some European Biological Indicators", 12 Health Laboratory Science at 225-229 (1975).

*Diack and Vac Controls*, "New Developments in EO Sterilization", 21(5) Aorn Journal at 962 (1975).

*Diack and Vac Controls*, "Smith & Underwood" advertisement for Diack and VAC Controls, 21(2) Aorn Journal (1975).

*Four Autoclave Sterilization Indicators*, "Aseptic--Thermo Indicator Company", 53 Hospital Topics at 42 (1975).

K. Kereluk, "Quality Control in Sterilization Procedures: Biological Indicators", 53 Hospital Topics at 25-39 (1975).

Irving J. Pflug, "Performance of Biological Indicators Designed for Monitoring", (1975).

*Sybron/Castle*, "UniSpore Biological Indicators", Castle/Sybron Service Bulletin at 1035 (1975).

John R. Gillis, "Biological Indicators for Steam Sterilization Process Monitoring", 29 Bulletin Parenteral Drug Assoc. at 111-121 (1975).

Andrew W. Munster, "Combating Hospital Infections: New Concepts for the '70's", 49 Infection Control at 85-89 (1975).

James Whitbourne and Keith West, "Sterility Testing: How Appropriate for the Hospital", 10 Medical Instrumentation at 291-292 (1976).

Wm. C. Beck, "A New Instrument for Measuring and for Monitoring the Time and Temperature of Steam Sterilizers", 45(4) Guthrie at 197-204 (1976).

*Bio-Medical Sciences, Inc.*, "Thermalog-S Steam Sterilization Monitor", Laboratory Bulletin (1976).

*Bio-Medical Sciences, Inc.*, "Thermalog-S Steam Sterilization Integrator", Technical Monigraph at 2-11 (1976).

R. J. Witonsky, "An Overview of Thermalog-S" (Bio-Medical Sciences, Inc.), BMS Report at 1-19 (1976).

William C. Beck, "A New Integrator for Monitoring (List continued on next page.)

OTHER PUBLICATIONS

Time and Temperature of Steam Sterlizers", 10(6) Med. Inst. Nov.-Dec. at 293-296 (1976).

R. J. Witonsky, "A New Tool for the Validation of the Sterilization of Parenterals", 31 Bulletin of the Parenteral Drug Assoc. at 274 (1977).

M. Furuhashi and T. Miyamae, "A New Method to Confirm the Efficiency of Steam Sterilization Relation Between Thermalog-S Integrator and the Thermal Destruction of Microbiol Spores" (translation only), Presentation at the 51st Meeting of the Japanese Association for Infectious Diseases (1977).

M. Gay, "Les Indicateurs Biologiques De Sterilisation" (no translation), 32(5) J. Pharm. De Belgique at 520-524 (1977).

G. Franchi and E. Lencioni, "La Sicurezza Di Un Processo Di Sterilizzazione A Vapore In Campo Farmaceutico Mediante L'Impiego Degli Indicatori Thermalog-S" (and translation), 117 Boll. Chim. Farm. at 620-626 (1978).

HIMA Report 78-4.4, "HIMA Medical Device Sterilization Monographs: Biological and Chemical Indicators; Manufacturing, Engineering and Quality Assurance Section Task Force on Biological & Chemical Indicators", Health Industry Manufacturers Assoc., August (1978).

Cheri-Ho Lee, Thomas J. Montville and Anthony J. Sinskey, "Comparison of the Efficacy of Steam Sterilization Indicators", 37(6) Appl. Environ. Microbiol. at 1113 (1979).

M. Karki, "Performance Standards for Chemical Indicators", 52(2) Score at 19 (1980).

Robert J. Witonsky, "Chemical Indicators, More Sense, Less Dollars", Speech at 213-224 circa (1980).

Peter Jancke, "Superheated Steam in Porous Load Sterilizers", circa (1980).

R. A. Caputo and C. C. Mascoli, "The Design and Use of Biological Indicators for Sterilization-Cycle Validation", MD & DI at 23-26 and 42 (1980).

B. Kirk and R. Hambleton, "Evaluation of an Prototype Micro-Electronic Autoclave Cycle Integrator", 33 J. Pharm. Pharmacol. at 69-74 (1981).

L. Joslyn, "Sterilization Process Efficiences as Measured by Biological Indicators Versus Physical Indicators", 22 Dev. Indust. Micro. at 341-343 and 345-347 (1981).

R. Hajjar and A. Cuine, "Validation Des Methodes De Sterilisation Per Voie Humide Et Par Voie Seche", Sci. Techn. Pharm. at 323-330 (1982).

J. C. Darbord, "Indicateurs Biologiques De Sterilisation Interet Et Limites", Sci. Techn. Pharm. at 331-334 (1982).

Bertha Yanis Litsky, Ph.D., "Private Evaluation: Chemical & Biological Steam Sterilization Indicator Evaluation", (1982).

Arthur Hirsch, Ph.D. and Stan Manne, M.B.A., "Bioequivalent Chemical Steam Sterilization Indicators", 18(5) Medical Instrumentation at 272-275 (1984).

Robert R. Reich and Brian G. Fitzpatrick, "Flash Sterilization", *Journal of Hospital Surgical Processing and Distribution*, May-Jun. at 60-63 (1985).

Brian G. Fitzpatrick and Robert R. Reich, "EtO Sterilization Monitoring", Journal of Healthcare Material Management at 32-35 (1986).

Brian G. Fitzpatrick and Robert R. Reich, "Sterilization Monitoring in Vacuum Steam Sterilizers", Journal of Healthcare Material Management at 82-85 (1986).

M. Callanquin, F. Bourillet, J. C. Darbord, R. Hajjar, S. Klein, A. Le Guyader, J. L. Mazert, P. Montenoise and J. L. Prugnaud, "Indicateurs Physicochimiques Et Biologiques En Sterilisation" (and translation), STP Pharma 3 at 148-154 (1987).

C. Couturier, V. Goury, J. M. Bellocq, M. Callanquin and J. C. Darbord, "[A] Study for Validation of Sterilization Indicators", Pharmacie Centrale des Hospitaux Paris (translation) Hospital Louis Mourier, Colombes (1989).

Patrick P. Caporino, "How Effective are Chemical and Biological Sterilization Indicators?", Journal of Healthcare Material Management at 32-44 (1991).

STEAM STERILIZATION INDICATOR

Matter enclosed in heavy brackets [ ] appears in the original patent but forms no part of this reissue specification; matter printed in italics indicates the additions made by reissue.

BACKGROUND OF THE INVENTION

This invention relates to steam sterilization indicators. More particularly, it relates to steam sterilization indicators which may be variable and/or adjustable in rate of indication at different sterilization temperatures.

Hospital utensils, such as surgical instruments, undergo sterilization for each use. In most instances, an autoclave is used to expose the utensils to live steam at various temperatures, usually between 250° F. and 275° F., although other temperatures are also used. The purpose for providing such sterilization is to destroy, with a high probability of success of safety factor, the microbial contamination which may be contained on these utensils. It is important to gauge the sterilization process so that the user may be assured that the utensils have, in fact, been subjected to those well-defined conditions necessary to render the material free of living organisms with a high probability of success. Several devices and techniques have been used to provide for such indication.

Of course, the materials which have been processed through the sterilizer could be biologically sampled to determine biological activity. However, this technique, while highly accurate, obviously would be very costly and impractical.

One very reliable method for providing indication of sterility is to utilize challenge spores which are placed in the autoclave during sterilization and then examined for their biological activity afterwards. For steam sterilizations, these challenge spores are usually Bacillus stearothermophilus and are used because they have a very high resistance to steam sterilization, thus giving a large safety factor. One example of this technique is set forth in U.S. Pat. No. 3,440,144, which provides a device for conducting such a test without the need to worry about subsequent contamination after the sterilization process is completed.

Another means to indicate sterilization is the use of sterilizer temperature recorder and gauges. These devices are usually attached to the sterilizer and measure the temperature in the sterilizer's exhaust line. While they are able to detect most malfunctions of the sterilizer, they cannot measure the condition at the place where the instruments were being sterilized.

A means for measuring the presence of steam, which is critical for steam sterilization, in an autoclave indicating tape. An example of such indicator tape is set forth in U.S. Pat. No. 2,889,799. A pressure-sensitive adhesive tape is used which includes a heat modifiable dye stuff impregnated thereon changing color at predetermined temperatures. However, these indicator tapes do not take into account the time that the instruments have been exposed to sterilizing temperature, and furthermore, are susceptible to prematurely changing color at low temperatures.

Another test which has been utilized is a so-called Bowie and Dick test. This test measures the uniformity of steam concentration in dressing packs. The test consists of several strips of autoclave indicating tape on a sheet of paper which is placed in the test pack. The tape on the paper is measured for uniformity of color change. One of the major limitations of this test is its failure to distinguish between high temperatures for a short period of time or low temperatures for a long period of time.

More recently, steam sterility indicators have been provided which integrate time, temperature and steam presence. Such a device is shown in U.S. Pat. No. 3,981,683. This device utilized a chemical such as 2-ethoxybenzamide or salicylamide as a fusible material. The melting points of these compounds are depressed by the presence of steam. A wicking strip is provided in close proximity to the chemical so that upon melt the chemical will slowly travel up the wick at a rate proportional to the sterilization temperature and time of exposure to such temperature, as well as the presence of steam. The device includes a cover strip which is a polymeric rate controlling film permitting water vapor (steam) to pass through thus depressing the melting point of the chemical. The strip cover and the wick are adhered to a backing by the use of an adhesive such as a silicone.

The device set forth in U.S. Pat. No. 3,981,683 is particularly useful where the exact temperature in the sterilization process it unknown. If it were known that the apparatus to be sterilized was an exact temperature, for example 250° F., then the stabilizer could be run for an exact amount of time so that the user could be assured of sterilization within a certain safety factor. However, without fitting the autoclave with some highly sophisticated and accurate monitoring equipment, it is impossible to know whether all areas of the autoclave are uniform at the same temperature. It is well known that the temperature of items being sterilized can vary due to many variables such as air entrapment, penetration of steam through packing material and position within the autoclave. Therefore, due to this unknown variable of temperature, it is a common practice for the microbiologist to investigate how a controlled change of temperature will affect the kill of the microorganism. He would do this by repeating the microbial death rate experiment at temperatures other than 250° F. After completing these experiments at other temperatures, a relationship can be obtained where the amount of time required to produce say $10^{-5}$ probability of surviving microorganisms, since this or some other safety factor producing a non-sterile item can be calculated. FIG. 3 shows an example of what the relationship of kill time vs. temperature might look like. The slope of the line is typical for microbial death rates, and, as can be seen, it is highly temperature sensitive. The death rate might be slowed down by a factor of 10 with a decrease of only 18° F. Conversely, an increase in temperature of only 18° F., will require only 1/10 the sterilization time. In other words, sterilizing to a probability of $10^{-5}$ in the example in FIG. 3 requires a 110 minutes at 232° F., 11 minutes at 250° F., and 1.1 minutes at 268° F. This value of 18° F. has been called the Z value and is defined as the number of degrees that are required to traverse a thermal death rate curve by one log. Thus this Z value becomes important when estimating spore death at different temperatures. This relationship has been defined mathmatically through the following equation:

$$t=(F_t)\times 10^{[(250-T)/Z]}$$

where t = the amount of time required at the actual process temperature (T).

In other words, it would require t minutes at temperature T in order to do the equivalent amount of sterilization as $F_o$ minutes at 250° F. (the reference temperature for steam sterilization). While a Z value of 18° F. is typical, it may vary quite often from between 16° F. to 23° F., and other values, depending on the type of microorganism, the pH and salt concentration as well as other variables. Therefore, if an adequate sterilization process is to be described, you must not only know the relative resistance at 250° F., but also the relative resistance at other temperatures. Thus the Z values must be known.

The graph in FIG. 4 graphically illustrates how a change in Z value can affect the sterilization times required at temperatures other than 250° F. Notice the different slopes of the lines for the various Z values. By using the standard sterilization equation set forth above, you can calculate that if Z is equal to 23° F., a time of 81.5 minutes is required at 230° F. to obtain an $F_o$ of 11 minutes. Conversely, for the same $F_o$, the time would have to be increased to 195.5 minutes at 230° F. for a Z value equal to 16° F. Thus it may be seen that, at temperatures lower than 250° F., as the Z value decreases, the kill time at predetermined temperatures increases.

The device set forth in U.S. Pat. No. 3,981,683 provides an indicator which is useful in a steam sterility process for spores having a Z value of 18° F., but it is not very flexible in terms of measuring sterilization of devices contaminated with spores with other Z values. Furthermore, it is a rather long device, thus materials are wasted.

OBJECTS OF THE INVENTION

Accordingly, it is one object of this invention to provide an improved steam sterilization indicator.

It is another object of this invention to provide an improved indicator which integrates time and temperature in the presence of steam.

It is a further object of this invention to provide a steam sterilization indicator which may be made variable in rate indication for tracking the kill time of various microorganisms at various temperatures.

It is still another object of this invention to provide a steam sterilization indicator which uses less materials than many prior art indicators.

It is another object of this invention to provide a steam sterilization indicator which is easily and cheaply manufactured.

It is a further object of this invention to provide a steam sterilization indicator which is adapted to slowly integrate time and temperature in the presence of steam so that the device may be made shorter, thus using fewer materials.

It is still another object of this invention to provide a sterilization indicator with an additional safety margin but still clearly tracks the kill time of microbes at various temperatures.

SUMMARY OF THE INVENTION

In accordance with one form of this invention there is provided a steam sterilization indicator which includes a tablet made of a fusible material and an amount of a binder. The fusible material is meltable at and above a predetermined temperature in the presence of substantially saturated steam. A wicking strip having one end in close proximity to the tablet is mounted on a backing. The backing also receives the tablet. In a steam environment, when predetermined temperature of melt is reached for the tablet, the fusible material moves along the strip at a rate proportional to the integration of time and temperature. The binder holds the fusible material in tablet form and further provides a mechanism for altering the rate of movement of the fusible material along the strip in proportion to the amount of binder used. As acrylic adhesive may be used to adhere the strip to the backing, as well as a transparent cover layer to the backing. The acrylic will further alter the movement of the fusible material along the strip.

BRIEF DESCRIPTION OF THE DRAWINGS

The subject matter which is regarded as the invention is set forth in the appended claims. The invention itself, however, together with further objects and advantages thereof, may be better understood with reference to the following description taken in conjunction with the accompanying drawings in which:

DESCRIPTION OF THE PREFERRED EMBODIMENT

Figure 1:
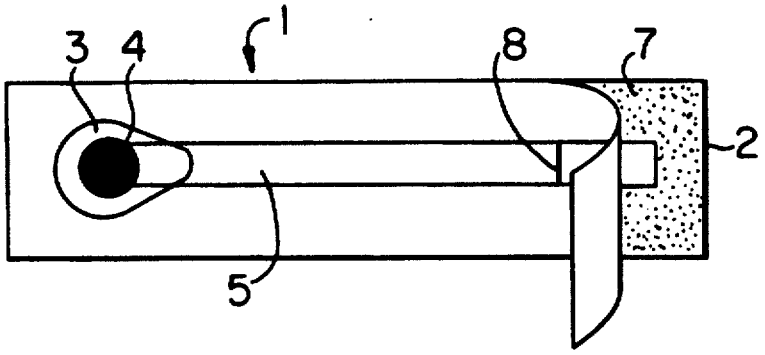
FIG. 1 is a plan view of the indicator incorporating the present invention with a portion of the cover peeled back.

Referring now more particularly to FIG. 1, there is provided steam sterilization indicator 1 which indicates that an environment or utensils in close proximity to it, has undergone proper steam sterilization. The device includes backing 2 which may be made of a metallic material acting as a good moisture barrier. In the preferred embodiment, the backing 2 is constructed of 3 mil thickness dead soft aluminum. The backing acts as a carrier or substrate for tablet 4 and wicking strip 5. The aluminum backing includes embossment or depression 3 near one of its ends for receiving the temperature and moisture sensitive tablet 4. Tablet 4 is made primarily from a chemical which melts or fuses at a predetermined temperature and above. However, its melt temperature is depressed somewhat in the presence of saturated stream. In the preferred embodiment, the chemical is salicylamide.

In order to increase manufacturing efficiency, i.e., placing the chemical in the embossment in the backing, it is desirable to maintain the chemical in tablet form. To do this and to provide the surprising results as will be described below, an amount of a binder is added to the temperature and moisture sensitive chemical. In the preferred embodiment of this invention the binder utilized is [polyvinylpyrrolidine] *polyvinylpyrrolidone* (PVP). The table also includes other constituents which are known to those skilled in the art of manufacturing tablets and may include such materials as talc and syloic.

In order to provide a color indication on strip 5 which will be described below, tablet 4 may also include a heat stable soluble dye which wicks onto and moves along strip 5 so long as the temperature and moisture content are sufficient to maintain the fusible chemical in its liquid state. Dyes such as Spirit Soluble Fast Black RE and Spirit Soluble Orange RR, both available from BASF Wyandotte Company, are suitable dyes.

The device is covered by *a* clear plastic cover layer [6], which in this embodiment is a 2 mil thickness unoriented polypropylene film, one form of which is available from the Exxon Corporation as Extrel 50. This clear layer enables one to see the position of the color front along wick 5. It also provides a controlled exposure of the temperature and moisture sensitive chemical to the steam since the polypropylene is slowly permeable to moisture transmission. The cover layer [6] as well as indicator strip 5 is adhered to the backing 2 by an adhesive 7, which in the preferred embodiment is an acrylic adhesive. One such acrylic adhesive which has been utilized is 3M 467, available from Minnesota Mining & Manufacturing Company. The importance of the use of the acrylic adhesive as well as the binder in the tablet will be made more clear below.

Wicking strip 5 is normally a porous material capable of wicking a liquid by capillary action. In this embodiment, the wick was made of Whatman 1 Chrome, available from the Whatman Company. It is placed either in contact with or nearly in contact with tablet 4 such that one end of the strip is within embossment 3. The wicking strip absorbs the melted chemical and carries the dye down the strip so long as the temperature is high enough and steam is present in a sufficient density. The rate of movement of the color front as well as the kill rate of microbes results from an integration of time and temperature so that this device is useful as various temperatures. That is, the time required for the color front to move a certain fixed distance is very temperature dependent. The same is true for the kill time of microbes. Then the color front on the strip reaches a certain position on the indicator, such as that indicated at position 8, it is assumed that the environment has undergone proper sterilization, i.e., the probability that all of the microbes present have been killed is, say, 0.99999. The device may be covered on the outside of the clear plastic covering with another sheet of paper (not shown) having an elongated slot which provides for a visual indication of the strip. This paper may have various indicia thereon.

Figure 2:
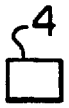
FIG. 2 is a side view of the tablet which is utilized in FIG. 1.
Figure 3:
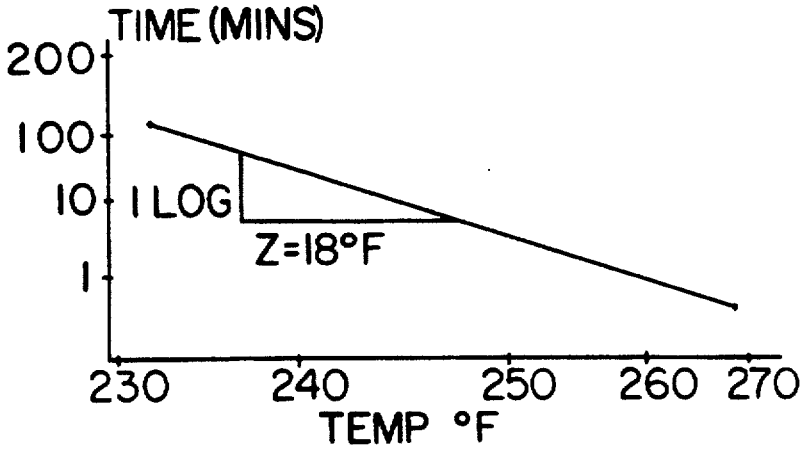
FIG. 3 is a graph of the death curve of the microbe C. sporogenes at various temperatures showing how the Z value is calculated.
Figure 4:
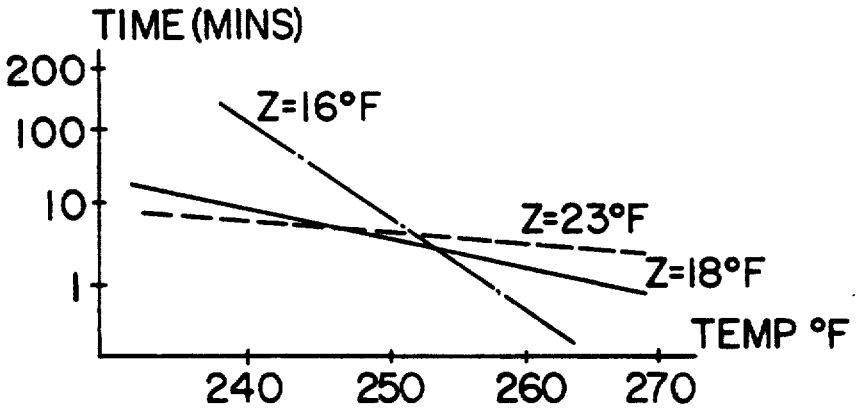
FIG. 4 is a graph depicting the effect of different Z values on thermal death curves of microbes.

The device thus described operates in a similar manner with the device described in U.S. Pat. No. 3,981,683 filed Sept. 21, 1976, and the description in that patent is hereby incorporated by reference. However, the present device includes at least two important differences in composition and several important differences in operation. One of the differences in composition between the device of the subject invention and the previously patented device is that the temperature and moisture dependent chemical is in tablet form rather than just a glob of material. An acceptable tablet is shown in FIG. 2. It is much easier to deposit a solid tablet into the embossment 3 during the manufacturing of the device. Furthermore, the exact quantity of chemical may thus be inserted easily into the embossment.

As stated previously, a binder such as PVP was utilized to hold the chemical in tablet form in order to provide this improved manufacturing process. In doing so, a surprising result occurred. It was found that by the use of this binder a programmable device could be manufactured which has a color movement rate proportional to the percentage of binder contained in the tablet. Furthermore, an indicator which follows the rate of kill of microbes having various Z values could be obtained by varying the percentage of binder. The following table shows a comparison of kill times for a microbe having a Z value of 20.5 and a Z value of 18 and the run times along a strip 11.2 mm long utilizing a device incorporating the subject invention having salicylamide chemical with varying percentages of PVP binders.

TABLE 1

| | Kill Times (Mins.) | | Indicator Times (Mins.) | | | |
|---|---|---|---|---|---|---|
| Temp. | Z = 20.5 | Z = 18 | 0% | 1% | 2% | 3% PVP |
| 230 | 113.5 | 155.0 | 93.7 | 133.0 | 174 | 210 |
| 235 | 64.7 | 81.8 | 58 | 71.5 | 85 | 111 |
| 240 | 36.9 | 43.1 | 35 | 38.5 | 44 | 48 |
| 245 | 21.0 | 22.7 | 21.7 | 21.5 | 23.5 | 26 |
| 250 | 12.0 | 12.0 | 13.0 | 12.5 | 13.0 | 13 |
| 255 | 6.84 | 6.3 | 8.0 | 7.5 | 7.7 | 7 |
| 260 | 3.90 | 3.34 | 4.9 | 4.8 | 4.7 | 4.4 |
| 265 | 2.23 | 1.76 | 2.9 | 2.9 | 3.0 | 3.2 |
| 270 | 1.27 | 0.93 | 1.8 | 1.9 | 2.1 | 2.6 |

Table I shows the indicator times of the device of FIG. 1 using from 0% PVP binder to 3% binder at various temperatures. As can be seen from the chart in Table I, the indicator times may be increased by increasing the amount of binder in the tablet so as to conform with the Z value of the particular microbe which is to be killed.

Figure 5:
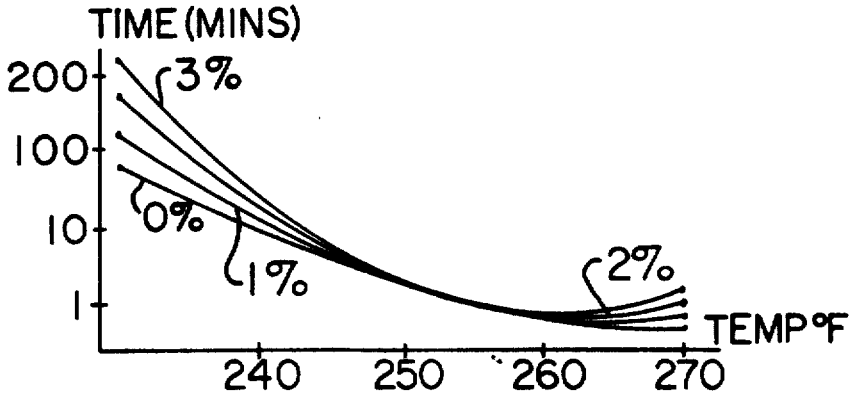
FIG. 5 is a graph showing the running time of the indicator shown in FIG. 1 at several temperatures with various amounts of binder in the tablet.

A graphic example of how the Z value of the device may be altered by adding or changing the binder content may be seen from the graph in FIG. 5 which again shows three devices each having binders from 0 to 3%. The graph shows that the time for the device to run to completion increases, particularly at the lower temperatures, as the percentage of binder increases. As it further may be seen from FIG. 5, the changes in the binder content affects the range between 230° F. and 250° F. and the range of 260° F. to 270° F., much more than at the mid-range.

Further, as can be seen, adding a binder introduces a safety factor in the operation of the indicator. One may notice from Table I that a device with 0% binder to monitor a sterilization process with Z value of 20° F. will run in 93.7 minutes, while the kill time of the particular microbe is 113.5 minutes, thus giving a false and potentially dangerous indication of kill. However, it should be noted that by adding 1% binder the indicator times are lengthened such that there is a slight margin of safety at all temperatures, and therefore this device will never indicate sterilization prematurely. For the bacteria which has a Z of 18° F., a 2% binder would be utilized. It should be recognized from FIG. 5 and from Table I that at temperatures above 260° F. the lines of the various percentage binders tend to come together and substantially flatten out. However, it should be noted that the lines are always curving upwardly and on the safety side of any bacteria with such a Z curve and these should never provide premature indication of sterilization.

Figure 6:
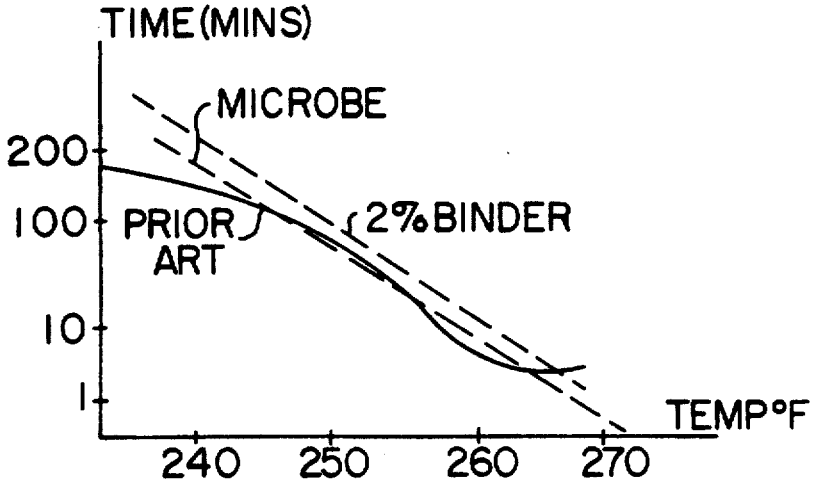
FIG. 6 depicts the run time of one of the devices of the subject invention at various temperatures compared with a prior art device and the thermal death curve of a microbe.

FIG. 6 shows a graph of a comparison of the device of the subject invention utilizing a 2% binder in comparison with the thermal death curve of B. stearothermophilus and a prior art device as set forth in U.S. Pat. No. 3,981,683. As can be seen, the device which utilizes a 2% binder PVP in salicylamide substantially tracks the death curve of B. stearothermophilus, but on the high safe side. However, as can be seen, the prior art device particularly at low temperature tracks the bacteria death curve on the lower unsafe side, and also shows a low "knee" at some high temperatures.

It has further been found that one may lower the temperature dependent reaction rate by utilizing an acrylic adhesive in the place of a silicone pressure sensitive adhesive which was used in the device set forth in U.S. Pat. No. 3,981,683. The adhesive is used to hold the wick and the cover onto the backing. It has also been found that there was a gross change in reaction rate of the device whereby its equivalent Z value was decreased from 26° F. to 20° F. by replacing the silicone base pressure sensitive adhesive with an acrylic. Table II below shows the actual time required for the device of the subject invention to indicate sterilization using a silicone adhesive, namely Densil 2078, provided by Dennison, Inc. and two brands of acrylics, namely Dencryl 410, also provided by Dennison, Inc., and Tackmaster 535, provided by the National Starch and Chemical Corporation.

TABLE II

| | Indicator Times (Mins.) | | |
|---|---|---|---|
| Temp. | Silicone | Acrylic I | Acrylic II |
| 230° F. | 110 | 137 | 154 |
| 240° F. | 29 | 51 | 53 |
| 250° F. | 12 | 12 | 12 |
| 260° F. | 5.1 | 4.7 | 3.6 |
| 270° F. | 3.1 | 1.85 | 1.9 |
| Approx. Equivalent Z Values | 26.0° F. | 20.9° F. | 20.0° F. |

Thus it may seem that the indicator times are substantially lengthened and it may be seen that the equivalent Z value was decreased by approximately 5° to 6° by utilizing an acrylic in place of the silicone adhesive. It is not understood exactly what phenomenon is causing these changes in equivalent Z value and thus in indicator times; however, it is quite possible that the acrylic may be reacting with the salicylamide in some way to slow down the movement of the color front or the acrylic may be acting as a better seal as compared to the silicone to prevent some of the steam from penetrating into the chemical, thus affecting the depression in the melt point.

Thus, it may be seen that there is provided an improved steam sterilization indicator which may be made adjustable in its rate of indication and further may be provided with an additional safety margin over the prior art.

Furthermore, since the rates of indicator movement are slowed, the device may be made substantially shorter than the device described in U.S. Pat. No. 3,981,683, thus saving materials. The length of the device described in U.S. Pat. No. 3,981,683 is approximately 4 inches, while the length of a device incorporating one embodiment of the subject invention is approximately 2 inches.

From the foregoing description of the preferred embodiment of the invention it will be apparent that many modifications may be made therein. It should be understood, however, that this embodiment is intended merely as an exemplification of the invention and that the invention is not limited thereto. It should be understood, therefore, that it is intended that in the appended claims to cover all such modifications in the true spirit and scope of the invention.

I claim:

1. A steam sterilization indicator comprising:

a tablet including a fusible material and a binder, said fusible material meltable at a predetermined temperature in the presence of substantially saturated steam, the melting point of said fusible material being substantially lower in the presence of saturated steam than when dry;

a wicking strip having one end in close proximity to said tablet whereupon attainment of said predetermined temperature, said fusible material melts and moves along said strip at a rate proportional to the temperature of said saturated steam;

a steam permeable membrane covering said tablet and said wicking strip, said binder holding said fusible material in tablet form prior to attainment of said predetermined temperature and further providing a mechanism for altering the rate movement of said fusible material along said wicking strip as a function of the amount of binder used for certain temperature ranges, such rate of movement being similar to spore death kinetics;

a backing; and an acrylic adhesive, wherein said backing and said membrane enclose said tablet and said strip and said acrylic adhesive holds said membrane and said strip to said backing, said acrylic adhesive acting to further alter the rate of movement of said fusible material along said strip.

2. The indicator as set forth in claim 1 wherein said fusible material is salicylamide.

3. The indicator as set forth in claim 1 wherein said binder is [polyvinylpyrrolidine] *polyvinylpyrrolidone.*

4. The indicator as set forth in claim 1 further including a dye in said tablet for providing a moving color front on said strip.

5. An indicator as set forth in claim 4 wherein said dye is taken from the group consisting of Spirit Soluble Fast Black RE and Spirit Soluble Orange RR.

6. The device as set forth in claim 1 wherein said amount of binder is no greater than 3% by weight of said tablet.

7. The device as set forth in claim 1 wherein the amount of said binder is within the range of from 1% to 3% by weight of said tablet.

8. An indicator as set forth in claim 1 wherein at least a portion of said membrane is transparent.

9. A steam sterilization indicator comprising:

a backing and a cover; said cover being permeable to steam; a fusible material being meltable at and above a said predetermined temperature; a wicking strip in substantial contact with said fusible material; said fusible material and said strip being located between said backing and said cover; said fusible material having its melting point substantially depressed in the presence of steam; said fusible material upon melting moving along said strip at a rate in proportion to the temperature of the saturated steam;

an acrylic adhesive holding said cover to said backing and said strip to said backing for altering the rate of movement of said fusible material along said strip.

10. An indicator set forth in claim 9 wherein said fusible material is salicylamide.

11. A device as set forth in claim [10] *12* wherein said binder is [polyvinylpyrrolidine] *polyvinylpyrrolidone.*

12. An indicator as set forth in claim 9 further including a binder added to said fusible material for further slowing down the rate of movement of said fusible material along said strip.

13. A steam sterilization indicator comprising:

a metallic backing having an embossment near one end thereof;

a tablet including both an amount of salicylamide which is fusible at a predetermined temperature and having the quality of having its melting point depressed in the presence of a substantial amount of moisture and an amount of polyvinylpyrrolidone, said tablet received in said embossment;

a wicking strip adhered to said metallic backing, said wicking strip having a portion thereof received in said embossment and in contact with said tablet;

a steam permeable cover having a transparent portion and received over said backing and adhered thereto by acrylic adhesive for further controlling the rate of movement of salicylamide along said strip; and a dye associated with said tablet for indicating the movement of said salicylamide along said wicking strip, said polyvinylpyrrolidone also controlling the rate of movement of molten salicylamide along said wicking strip.

* * * * *